United States Patent [19]

Fitch et al.

[11] Patent Number: 5,388,447
[45] Date of Patent: Feb. 14, 1995

[54] VISCOSITY MEASUREMENT APPARATUS

[75] Inventors: James C. Fitch, Tulsa; Kym Bergstrom, Broken Arrow, both of Okla.

[73] Assignee: Diagnetics, Inc., Tulsa, Okla.

[21] Appl. No.: 157,532

[22] Filed: Nov. 26, 1993

[51] Int. Cl.$^6$ ............................................. G01N 11/04
[52] U.S. Cl. .................................................. 73/54.14
[58] Field of Search .................. 73/54.14, 54.15, 54.18, 73/54.19

[56] References Cited

FOREIGN PATENT DOCUMENTS

| | | | |
|---|---|---|---|
| 248156 | 7/1966 | Austria | 73/54.15 |
| 12832 | 4/1972 | Japan | 73/54.14 |
| 21542 | 2/1983 | Japan | 73/54.14 |
| 624145 | 9/1978 | U.S.S.R. | 73/54.15 |
| 669269 | 6/1979 | U.S.S.R. | 73/54.15 |
| 709983 | 1/1980 | U.S.S.R. | 73/54.18 |

OTHER PUBLICATIONS

E. W. Schoder, "Hydraulics", pp. 244–246.
J. C. Fitch and J. B. Allred, "Hydraulic Fluid Analysis: Avoiding the Potential Pitfalls", *Hydraulics & Pneumatics* (Dec. 1987 & Jan. 1988).
Jim C. Fitch, "Theory, Design, and Performance Characteristics of a Direct–Reading Portable Solid Contaminant Analyzer" (1986).

*Primary Examiner*—Hezron E. Williams
*Assistant Examiner*—Joseph W. Roskos
*Attorney, Agent, or Firm*—Head & Johnson

[57] ABSTRACT

A viscosity measurement apparatus for measuring viscosity of a fluid under known pressure. A tube of known diameter and length allows the fluid to pass therethrough. A closed chamber is in fluid communication with the tube. A piston, sealably engaged with the chamber, may be moved by force of the fluid passing through the tube. A linear gauge measures the time required to move the piston. A mechanism is provided to reset the piston by forcing fluid back through the tube to empty the chamber to begin another measurement.

19 Claims, 2 Drawing Sheets

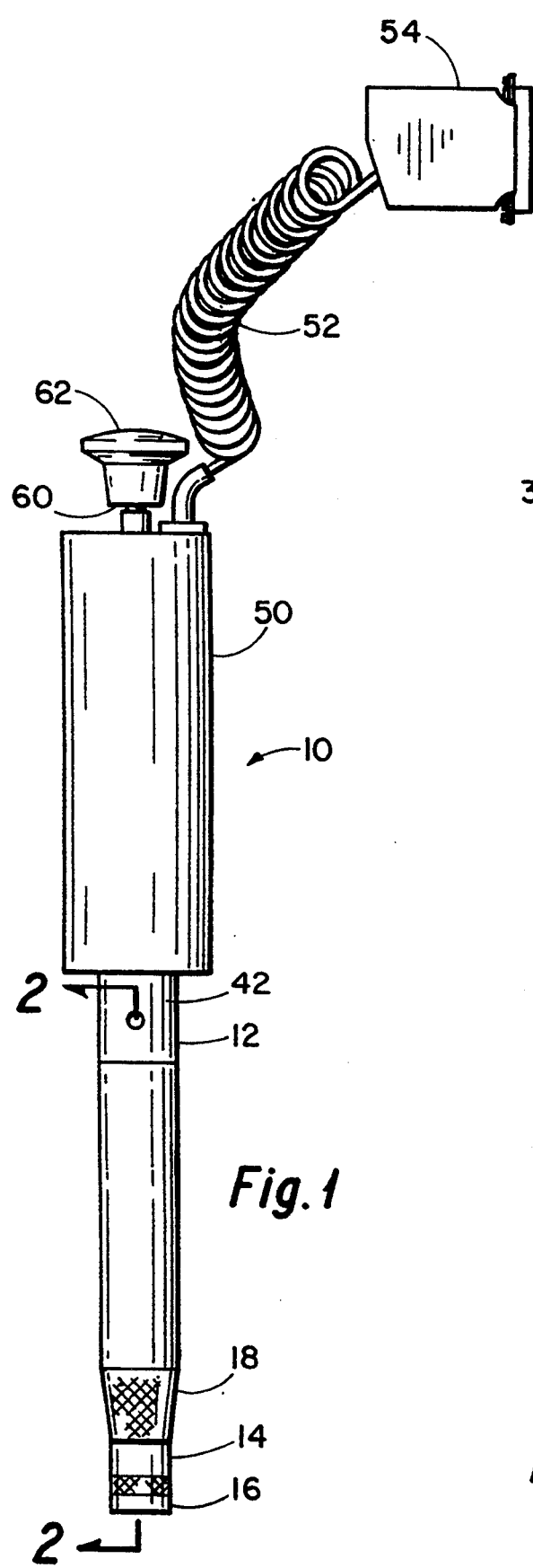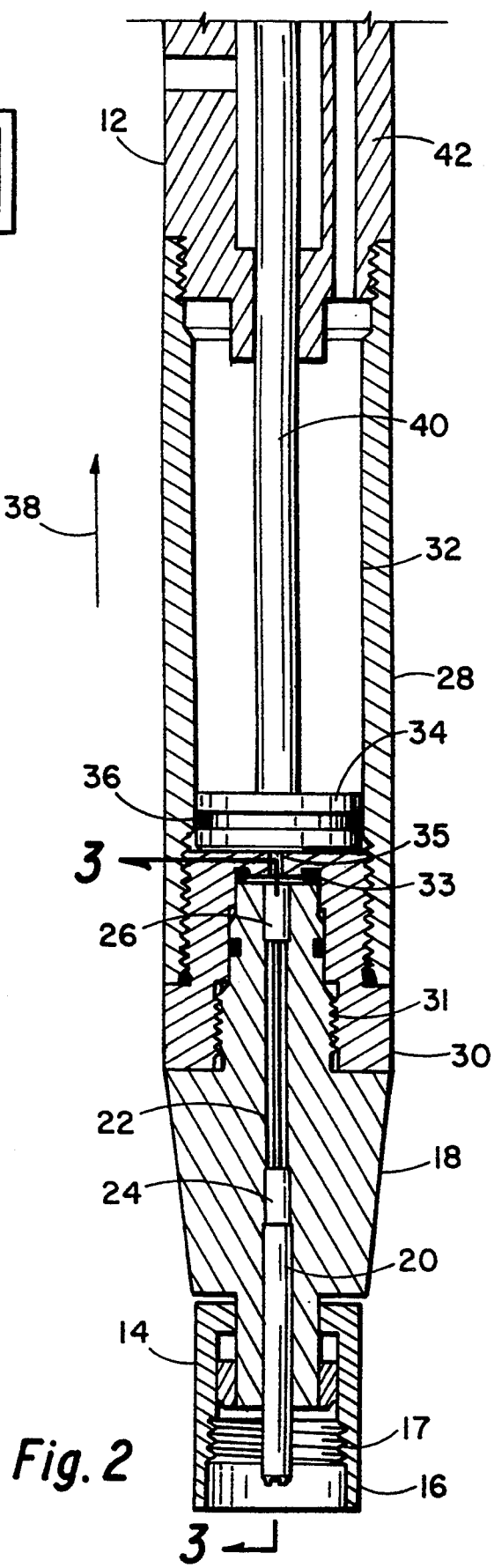

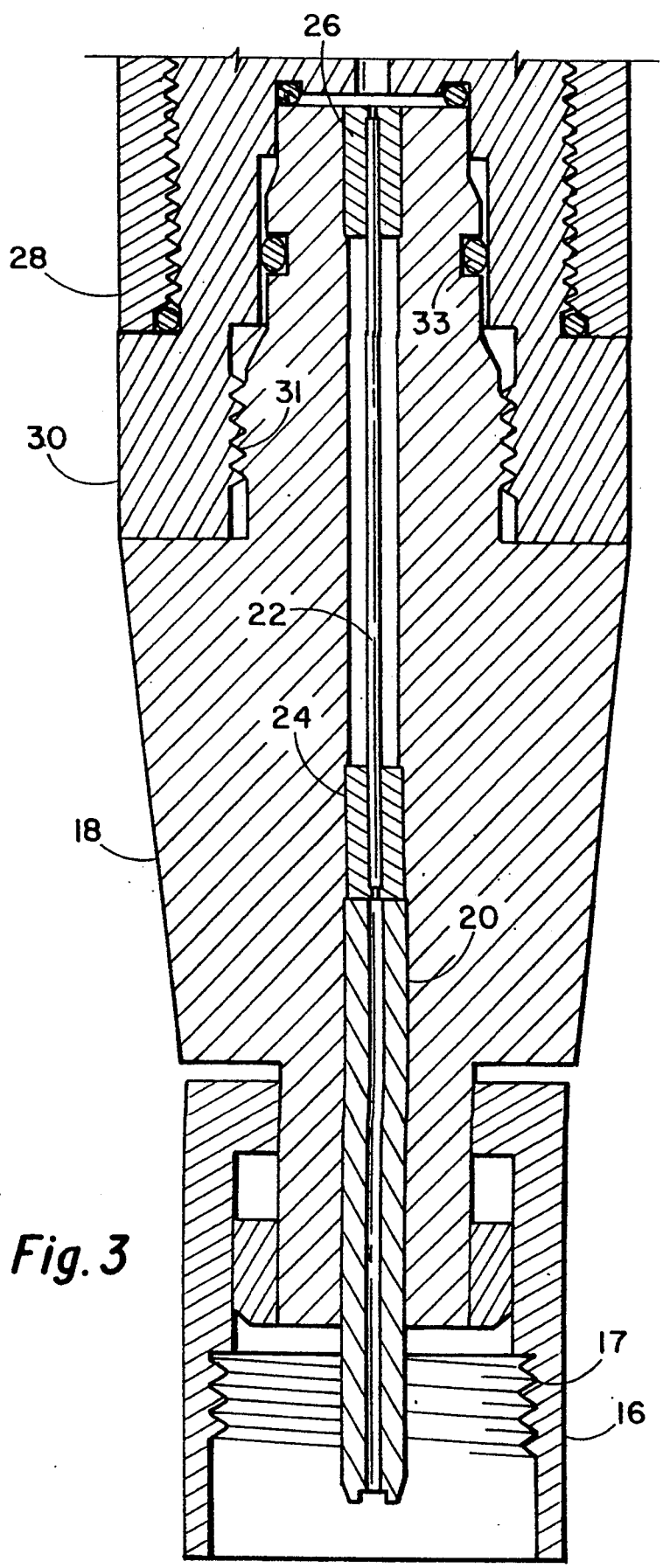
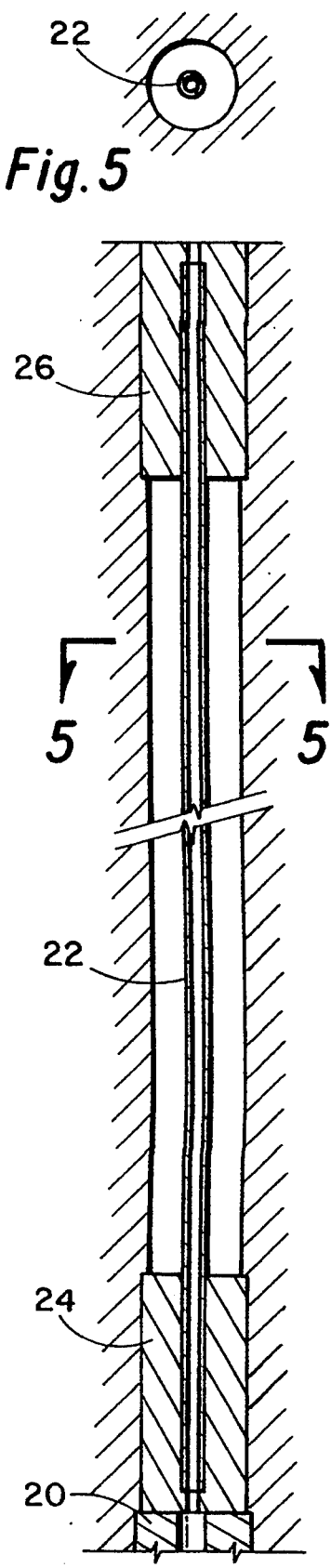
Fig. 3
Fig. 4
Fig. 5

VISCOSITY MEASUREMENT APPARATUS

BACKGROUND OF THE INVENTION

1. Field of the Invention.

The present invention relates to a viscosity measurement apparatus to measure the viscosity of fluid under pressure in a fluid system. In particular, the present invention relates to a viscosity measurement apparatus that may be utilized on-line in a fluid system and may thereafter be reset to initiate a further measurement.

2. Prior Art.

Viscosity, the resistance a fluid presents to flow, is often an important measurement. Viscosity is measured by observing the time required for a certain volume of the liquid to flow through a short tube of small bore. While it is often determined for scientific or technical purposes, the viscosity is important in industrial applications. As hydraulic fluid ages, viscosity increases slowly. These increases in viscosity are caused by fluid base and additive oxidation. Unusually high operating temperatures accelerate the process. Therefore, rapid swings in fluid viscosity may signal the presence of system hot spots. Generally, any swing in viscosity of 10% or more is an indication that the fluid is nearing the end of its useful life. If the viscosity of a fluid varies, it may indicate a problem with the fluid system. Accordingly, it is important to monitor the viscosity in a fluid system.

While it is well known to periodically draw a sample from the fluid system and subject it to testing, it is desirable to be able to determine the viscosity of the fluid on-line.

It is also desirable to be able to reset the measurement apparatus to take additional, periodic tests of the viscosity as desired.

It is also desirable to rapidly calculate the viscosity and be able to transfer or deliver this information for analysis.

It is also desirable to provide a lightweight and portable viscosity measurement apparatus.

SUMMARY OF THE INVENTION

The present invention is directed to a viscosity measurement apparatus including an elongated body which may be attached to a sampling valve of a fluid system under pressure. A fitting is attached to an elongated viscosity probe body for connection to the sampling valve. Extending through an opening in the viscosity probe body is a first needle tube in communication with a second needle tube. The second needle tube is held in place within the probe body with a pair of sleeves which press-fit in the opening of the probe body. The needle tubes are of a known inside diameter and of a known length.

The probe body, in turn, is connected to a chamber body by an internally and externally threaded nut. The internal threads of the nut engage with threads on the probe body. The external threads of the nut engage with the chamber body.

The chamber body includes a cylindrical chamber in fluid communication with the second needle tube. Accordingly, fluid passing through the needle tubes will thereafter enter the chamber by passing through a passageway in the nut.

A piston sealably engaged with the chamber is allowed to reciprocate within the cylindrical chamber. The pressure from fluid passing through the needle tubes will move the piston away from the needle tubes. The piston is connected to a piston rod axially aligned with the cylindrical chamber so that movement of the piston translates into movement of the piston rod.

The piston rod is, in turn, connected to a linear gauge so that movement of the piston rod will be detected and measured by the linear gauge. By observing the time required to move the piston and by incorporating the temperature and pressure of the fluid, the absolute viscosity of the fluid is determined. If the density of the fluid is known, the kinematic viscosity of the fluid can be calculated.

A mechanism is provided to reset the linear gauge so that additional measurements may thereafter be taken. The piston rod is connected to an extension extending from and through the body of the apparatus and terminating in a plunger handle outside of the body.

Once a measurement has been taken, the apparatus may be reset. The plunger handle will be held by the operator and moved back toward the probe body containing the needle tubes. This action will force the piston back toward the needle tubes, thereby forcing all fluid in the chamber back through the needle tubes and back out of the apparatus. Once the piston has been moved back, all fluid will be out of the chamber. Thereafter, another measurement may be taken.

BRIEF DESCRIPTION OF THE DRAWINGS

FIG. 1 is a perspective view of a viscosity measurement apparatus constructed in accordance with the present invention;

FIG. 2 is a sectional view of the viscosity measurement apparatus taken along section line 2—2 of FIG. 1;

FIG. 3 is a sectional view of the viscosity measurement apparatus taken along section line 3—3 of FIG. 2;

FIG. 4 is a partial, sectional view illustrating a needle tube for passage of fluid in the viscosity measurement apparatus as shown in FIG. 1; and FIG. 5 is a sectional view taken along section line 5—5 of FIG. 4.

DETAILED DESCRIPTION OF THE PREFERRED EMBODIMENT

Referring to the drawings in detail, FIG. 1 shows a perspective view of a viscosity measurement apparatus 10 constructed in accordance with the present invention. The apparatus operates by measuring the flow rate of a fluid through a resistive columnar passage maintaining laminar flow. The apparatus 10 includes an elongated body 12 which may be attached to a sampling valve (not shown) of a fluid system. The fluid system will contain fluid under known pressure. The apparatus may be connected to the sampling valve by means of friction fit or screw threaded fitting 14. Once connected, fluid from the system may pass into said fitting. The fitting 14 may include a connection nut 16 having internal threads 17. The connection nut 16 is connected to an elongated viscosity probe body 18.

FIGS. 2 and 3 illustrate sectional views of the viscosity probe body 18.

Extending through an opening in the viscosity probe body 18 is a first needle tube 20 in fluid communication and axially aligned with a second needle tube 22. The second needle tube 22 is held in place within the probe body 18 by a pair of sleeves 24 and 26. The sleeves friction- or press-fit into an opening in the probe body and are seen most clearly in the enlarged detail of the innermost passage shown in FIG. 4. FIG. 5 shows a sectional view taken along FIG. 4 illustrating the second needle tube 22 suspended within the opening in the probe body. The needle tube 22 is of a known inside diameter and known length. Second tube 22 is of significantly smaller diameter than tube 20 thereby minimizing any effect based on tube 20. In one embodiment, the needle tube 22 has an inner diameter of 400 microns.

It will be understood that while a tube 22 is used in the present embodiment for passage through a known diameter, a restricted orifice might also be employed.

As best seen in FIGS. 2 and 3, the probe body 18 is connected to a chamber body 28 by an internally and externally threaded nut 30. The internal threads 31 of the nut 30 engage with threads on the probe body 18. O-rings 33 may be used to assist in maintaining a seal between the nut 30 and probe body.

The chamber body 28 includes a cylindrical chamber 32 which is in fluid communication with the second needle tube 22. Accordingly, fluid passing through the needle tubes will thereafter enter the chamber 32 by passing through a passageway 35 in the nut 30. A piston 34 sealably engaged with the chamber is allowed to reciprocate within the cylindrical chamber. As seen in FIG. 2, the piston 34 may include an O-ring 36 to assure a fluid-tight seal with the walls of the chamber.

Because the probe body, threaded nut, and chamber body 28 are all threadably connected, the apparatus may be disassembled easily for cleaning and maintenance.

The piston 34 is shown in FIG. 2 in a position prior to beginning a viscosity measurement reading. The piston 34 abuts against the threaded nut 30 so that the passageway 35 is closed. When a measurement is initiated, fluid will be allowed to flow through the needle tubes. Fluid passing through the needle tube will move the piston 34 away from the needle tubes in the direction shown by the arrow 38. The piston 34 is, in turn, connected to a piston rod 40 axially aligned with the cylindrical chamber 32 so that movement of the piston translates into movement of the piston rod.

With continuing reference to FIG. 2 and also reference to FIG. 1, the piston rod 40 is connected to a linear gauge 50 through a gauge adapter 42. The gauge adapter 42 includes an axial opening therethrough so that movement of the piston rod 40 will be measured by the linear gauge 50. The linear gauge is a displacement transducer. By measuring the time and distance moved, the velocity is determined.

The testing is continued until a stable velocity is reached. By continuing until a stable velocity is reached, it will minimize problems of cross contamination between samples.

By observing the time required to move the piston and by incorporating the temperature and pressure of the fluid, the absolute viscosity of the fluid is determined.

According to Newton's law of viscosity, shear stress per unit area is proportional to the negative of the local velocity gradient and is expressed as:

$$w = -\mu \frac{dv_x}{dy} \quad (1)$$

where $\mu$ is fluid viscosity. This formula also suggests that shear stress occurs when the fluid acquires a certain amount of momentum, and there is relative movement between two adjacent layers of the fluid. The present invention, which measures the fluid's viscosity was developed based on this theory.

The apparatus allows testing fluids to flow at a known pressure difference. Since gauge pressure in the chamber prior to initiation of a measurement test is zero, the pressure difference will be the gauge pressure of the fluid system. By measuring the pressure difference and the volumetric flowrate, the viscosity can be obtained from the mathematical model derived below.

Suppose the fluid flows through the appropriate sized tube where boundary layer and end effect can be neglected. Velocity profile can be obtained by starting from the equation of motion:

$$\varrho \frac{Dv}{Dt} = -\nabla p - \nabla w + \varrho g \quad (2)$$

substitution of equation (1), eliminating zero terms, and simplifying the equation with reasonable assumptions such as steady state, constant pressure and constant specific weight, we obtain:

$$-\frac{dp}{dz} = \mu \frac{1}{R} \frac{d}{dr}\left(r \frac{dv_z}{dr}\right) \quad (3)$$

where z is the flow direction and r is the radius of the tube. Here p represents the combined effect of static pressure and gravitational force.

Integration twice with respect to r, and the use of the boundary conditions that (a) $v_\phi = 0$ at $r = R$, and (b) $v_\phi =$ finite at $r = 0$ gives velocity profile as:

$$v_z = \nabla \frac{pR^2}{4\mu L}\left(1 - \left(\frac{r}{R}\right)^2\right) \quad (4)$$

Integration of velocity distribution, that is:

$$Q = \int_0^R \int_0^{2\Pi} \frac{\nabla p R^2}{4\mu L}\left(1 - \left(\frac{r}{R}\right)^2\right) ds\, dr \quad (5)$$

we directly obtain the expression of viscosity as:

$$\mu = \frac{\Pi \nabla p R^4}{8 Q L} \quad (6)$$

where L is the length of the tube.

Substitution of L=1.500 (in) and R=206 ($\mu$m) into the equation, which are fixed in one embodiment of the apparatus, in equation (6), we can express the absolute viscosity in cgs (poise) units as:

$$\mu = 0.1289 \frac{\nabla p}{Q} \quad (7)$$

Additionally, if the density of the fluid is known, the kinematic viscosity of the fluid can be calculated.

The linear gauge of the viscosity measurement apparatus may be wired via wire 52 and plug 54 to a computer or other mechanism to calculate and display the results.

A mechanism is also provided to reset the piston and linear gauge so that additional measurements may be taken. The piston rod 40 is connected to an extension 60 extending from the elongated body 12 of the apparatus and terminating in a handle 62. As the piston rod 40 moves in the direction shown by arrow 38 in FIG. 2, the handle 62 will move away from the apparatus 10. Once a measurement has been taken, the apparatus 10 may be reset. The plunger handle 62 will be held by the operator (not shown) and moved back toward the position shown in FIG. 1. This action will force the piston 34 to move within the chamber back towards the needle tubes 20 and 22, thereby forcing all fluid in the chamber 32 back through the needle tubes and back out of the apparatus. All of the sample fluid will, thus, be expelled. Once the piston has moved back to the return position, all fluid will be out of the chamber and another measurement may be taken.

In order to use the apparatus 10, the user will enter a command to begin or "Run Test" on the computer or other control. The piston 34 will be in the position shown in FIG. 2. The user will then enter the temperature and pressure of the fluid into the computer or other control.

As an option, a heater device may be juxtaposed between the apparatus and the fluid system to heat the fluid to a precise, known temperature. Additionally, a temperature measurement device may be incorporated within the viscosity monitor to measure the temperature without operator intervention. The actual measurement begins when the user attaches the fitting 14 on to the sampling valve of the fluid system. As soon as the fitting is on the sampling valve, fluid under pressure is allowed to flow so that the test begins. The measurement time in the present embodiment ranges from 30 seconds to two minutes.

Whereas, the present invention has been described in relation to the drawings attached hereto, it should be understood that other and further modifications, apart from those shown or suggested herein, may be made within the spirit and scope of this invention.

What is claimed is:

1. A viscosity measurement apparatus for measuring the viscosity of a fluid under known pressure, which apparatus comprises:
   a tube of known diameter and length for allowing said fluid to pass therethrough;
   a closed chamber in fluid communication with said tube;
   means to move a piston sealably engaged with said chamber by force of said fluid passing through said tube;
   linear gauge means to measure the time required to move said piston; and
   means to calculate viscosity from said known pressure, said known tube diameter and length and from said linear gauge measurement.

2. A viscosity measurement apparatus as set forth in claim 1 including means to move said piston between a closed position wherein no fluid enters said chamber to an open position allowing fluid flow into said chamber.

3. A viscosity measurement apparatus as set forth in claim 1 wherein said tube is a needle and is retained within a probe body by a pair of sleeves.

4. A viscosity measurement apparatus as set forth in claim 3 wherein said fluid is within a fluid system and including connection means to connect said probe body to a port of said fluid system.

5. A viscosity measurement apparatus as set forth in claim including a piston rod extending from said piston.

6. A viscosity measurement apparatus as set forth in claim 1 including means to regulate the temperature of said fluid prior to entering said tube.

7. A viscosity measurement apparatus as set forth in claim 6 including means to automatically measure the temperature of said fluid prior to entering said tube.

8. A viscosity measurement apparatus as set forth in claim 5 wherein said means to reset said piston includes a plunger connected to said piston rod and axially aligned with said chamber.

9. A viscosity measurement apparatus as set forth in claim 1 wherein said fluid under known pressure is within a fluid system and including means to continuously monitor said fluid in-line in said fluid system.

10. A viscosity measurement apparatus as set forth in claim 1 including means to reset said piston by forcing said fluid back through said tube to empty said chamber to begin another said measurement.

11. A viscosity measurement apparatus for measuring the viscosity of a fluid under known pressure, which apparatus comprises:
    an orifice of known diameter and length for allowing said fluid to pass therethrough;
    a closed chamber in fluid communication with said orifice;
    means to move a piston sealably engaged with said chamber by force of said fluid passing through said orifice;
    linear gauge means to measure the time required to move said piston; and
    means to calculate viscosity from said known pressure, said known orifice diameter and length and from said linear gauge measurement 12. A viscosity measurement apparatus as set forth in claim 11 including means to reset said piston by forcing said fluid back through said orifice to empty said chamber to begin another said measurement.

13. A viscosity measurement apparatus is set forth in claim 12, wherein said means to reset said piston includes a plunger connected to said piston rod said plunger axially aligned with said chamber.

14. A viscosity measurement apparatus as set forth in claim 11 including means to move said piston between a closed position wherein no fluid enters said chamber and an open position allowing fluid flow into said chamber.

15. A viscosity measurement apparatus is set forth in claim 11 wherein said fluid is within a fluid system and including connection means to connect a probe body containing said orifice to a port of said fluid system.

16. A viscosity measurement apparatus is set forth in claim including a piston rod extending from said piston.

17. A viscosity measurement apparatus is set forth in claim 11 including means to regulate the temperature of said fluid prior to entering said orifice.

18. A viscosity measurement apparatus is set forth in claim 11 including means to automatically measure the temperature of said fluid prior to entering said orifice.

19. A method of measuring the viscosity of a fluid under known pressure, which method comprises:
    passing said fluid through a tube of known diameter and length;
    providing a closed chamber in fluid communication with said tube;
    moving a piston sealably engaged with said chamber by force of said fluid passing through said tube;
    measuring the time required to move said piston through use of a gauge; and
    calculating viscosity from said known pressure, said known diameter and length and from said gauge measurement.

* * * * *